(12) United States Patent
Chapman et al.

(10) Patent No.: US 8,417,539 B2
(45) Date of Patent: *Apr. 9, 2013

(54) MACHINE VISION AND SPECTROSCOPIC PHARMACEUTICAL VERIFICATION

(75) Inventors: Kenneth Wayne Chapman, Raleigh, NC (US); John E. Stranzl, Jr., Holly Springs, NC (US); Evan C. Cull, Durham, NC (US); Prasant Potuluri, Raleigh, NC (US); David J. Brady, Durham, NC (US)

(73) Assignee: Optopo Inc., Morrisville, NC (US)

( * ) Notice: Subject to any disclaimer, the term of this patent is extended or adjusted under 35 U.S.C. 154(b) by 1050 days.

This patent is subject to a terminal disclaimer.

(21) Appl. No.: 12/326,558

(22) Filed: Dec. 2, 2008

(65) Prior Publication Data

US 2009/0080735 A1    Mar. 26, 2009

Related U.S. Application Data

(63) Continuation-in-part of application No. 11/609,443, filed on Dec. 12, 2006, now Pat. No. 7,720,694, which is a continuation-in-part of application No. 11/454,923, filed on Jun. 19, 2006, now Pat. No. 7,218,395, which is a continuation-in-part of application No. 10/417,066, filed on Apr. 16, 2003, now Pat. No. 7,092,101, and a continuation-in-part of application No. 11/334,546, filed on Jan. 19, 2006, now Pat. No. 7,301,625.

(60) Provisional application No. 60/725,311, filed on Oct. 12, 2005, provisional application No. 60/811,101, filed on Jun. 6, 2006, provisional application No. 60/644,522, filed on Jan. 19, 2005, provisional application No. 60/705, 173, filed on Aug. 4, 2005.

(51) Int. Cl.
*G06Q 10/00* (2012.01)
*G06K 9/46* (2006.01)

(52) U.S. Cl.
USPC .............................................. 705/2; 382/190

(58) Field of Classification Search ........................ 705/2
See application file for complete search history.

(56) References Cited

U.S. PATENT DOCUMENTS

| | | | | |
|---|---|---|---|---|
| 5,365,343 A | * | 11/1994 | Knapp | 356/427 |
| 5,444,237 A | * | 8/1995 | Takizawa | 250/223 B |
| 6,535,637 B1 | * | 3/2003 | Wootton et al. | 382/190 |
| 7,218,395 B2 | * | 5/2007 | Kaye et al. | 356/301 |
| 2005/0095696 A9 | * | 5/2005 | Lemmo et al. | 435/287.1 |

* cited by examiner

*Primary Examiner* — Hiep V Nguyen
(74) *Attorney, Agent, or Firm* — John R. Kasha; Kasha Law LLC

(57) ABSTRACT

A pharmaceutical solid in a prescription vial is identified from an optical property of the pharmaceutical solid using light reflected from two different light sources. For each known pharmaceutical solid, an optical property of the known pharmaceutical solid is stored. The prescription vial is illuminated with a first light source and a first image is recorded. The prescription vial is then illuminated with a second light source and a second image is recorded. The first image and the second image are processed to find an optical property of the pharmaceutical solid. The optical property found is compared to the stored optical properties. The identity of the pharmaceutical solid is determined from the comparison. The first light source and the second light source are selected to remove artifacts of the prescription bottle or to enhance or suppress two-dimensional or three-dimensional effects on the surface of the pharmaceutical solid.

47 Claims, 4 Drawing Sheets

MACHINE VISION AND SPECTROSCOPIC PHARMACEUTICAL VERIFICATION

CROSS-REFERENCE TO RELATED APPLICATION

This application is a continuation-in-part application of U.S. patent application Ser. No. 11/609,443, filed Dec. 12, 2006 now U.S. Pat. No. 7,720,694 (the "'443 application"). The '443 application is a continuation-in-part application of U.S. patent application Ser. No. 11/454,923 (the "'923 application"), filed Jun. 19, 2006 now U.S. Pat. No. 7,218,395 (the "'395 patent"). The '923 application is a continuation-in-part application of U.S. patent application Ser. No. 10/417,066, filed Apr. 16, 2003 now U.S. Pat. No. 7,092,101 (the "'101 patent"), and a continuation-in-part application of U.S. patent application Ser. No. 11/334,546 (the "'546 application"), filed Jan. 19, 2006 now U.S. Pat. No. 7,301,625 (the "'625 patent"). The '923 application also claims the benefit of U.S. Provisional Patent Application No. 60/725,311, filed Oct. 12, 2005, and U.S. Provisional Patent Application No. 60/811,101, filed Jun. 6, 2006. The '546 application claims the benefit of U.S. Provisional Patent Application No. 60/644,522, filed Jan. 19, 2005, and U.S. Provisional Patent Application No. 60/705,173, filed Aug. 4, 2005. All of the above mentioned applications are incorporated by reference herein in their entireties.

BACKGROUND OF THE INVENTION

1. Field of the Invention

Embodiments of the present invention relate to systems and methods for prescription or pharmaceutical compound verification. More particularly, embodiments of the present invention relate to systems and methods for pharmaceutical verification using machine vision and spectroscopic analysis.

2. Background Information

Most states in the U.S. require that a registered pharmacist confirm whether a pharmaceutical delivered to a customer is indeed the pharmaceutical prescribed by the physician. A part of this confirmation is accomplished by the pharmacist visually inspecting the dispensed pharmaceutical to verify its correctness. In fact, pharmacists can spend as much as 50% of their time verifying prescriptions.

Despite the verification process, errors are not uncommon, especially during peak operating hours. For example, according to the National Association of Boards of Pharmacy, as many as 5% of the 3 billion prescriptions filled each year are incorrect. These erroneous prescriptions are responsible for as many as 7,000 deaths annually in the United States. Further, due to a steadily decreasing number of pharmacists, and an expected increase in the annual demand for prescriptions to nearly 5 billion, the number of instances in which a customer receives the wrong medication is anticipated to increase.

Not surprisingly, increasing prescription errors have resulted in a growing collection of consumer complaints about potentially serious errors such as wrong counts, wrong drugs, and/or wrong drug strengths. Drug strength is, for example, a quantification of the concentration or potency of the active ingredient of the drug. Thus, there is a strong need for a system to replace the present manual verification technique and to allow the verification and validation steps to be performed automatically and more reliably. A by-product of such an automatic verification system is freeing up pharmacists' time so they can provide better service to their customers.

Several conventional semi-automated prescription verification techniques have been developed to minimize errors associated with manual prescription verification. For example, conventional semi-automatic visual verification techniques rely on the pharmacists comparing an electronic image of the prescribed medication, i.e., a picture of the prescribed medication retrieved from a data library, to the actual medication that is to be dispensed to a customer. However, the visual difference between pharmaceuticals may be so subtle that errors are likely to occur even when comparing the contents of the prescription vial to a picture on a computer screen.

More objective and automated visual recognition techniques have also been applied to prescription verification. Such techniques use an imaging device and image processing algorithms to produce what is often referred to as machine vision. For example, U.S. Pat. No. 6,535,637 to Wootton et al. describes obtaining an image of the contents of a pharmaceutical container through the open top of the container, processing the image to isolate a pill, processing the image of the pill to extract a characteristic such as color, shape, size, finish, texture, or surface properties, and comparing the characteristic to known characteristics to identify the pill.

Spectroscopic techniques have also been used to verify dispensed pharmaceuticals. Spectroscopic techniques rely on the unique spectral signature exhibited by each pharmaceutical, such as a pill, tablet, capsule, gelcap, gel, and liquid. Representative, non-limiting spectroscopic techniques for pharmaceutical verification include Near-Infrared (NIR) spectroscopy, ultraviolet (UV) and visible spectroscopy, Raman spectroscopy, and Fourier Transform Infrared (FT-IR) spectroscopy.

Both machine vision and spectroscopic techniques of pharmaceutical verification have advantages and disadvantages. For example, a machine vision technique is likely to be fooled by counterfeit pharmaceuticals, while a spectroscopic technique is unlikely to have trouble spotting a counterfeit. Similarly, a spectroscopic technique might not be able to distinguish different strengths of the same pharmaceutical, while a machine vision technique can determine the different strengths by the shapes of the pills.

In view of the foregoing, it can be appreciated that a substantial need exists for systems and methods that can perform pharmaceutical verification using both machine vision and spectroscopic analysis.

BRIEF SUMMARY OF THE INVENTION

In one embodiment, a pharmaceutical solid in a prescription vial is identified from the shape of the pharmaceutical solid using light reflected from two different light sources. Shapes corresponding to known pharmaceutical solids are stored. The prescription vial is illuminated with a first light source and a first image is recorded. The prescription vial is then illuminated with a second light source and a second image is recorded. The first image and the second image are processed to find a shape of the pharmaceutical solid. The shape found is compared to one or more of the stored shapes. The identity of the pharmaceutical solid is determined from the comparison.

In another embodiment, a pharmaceutical solid in a prescription vial is identified from an optical property of the pharmaceutical solid using two light sources that effectively remove artifacts of the prescription vial. For each known pharmaceutical solid, an optical property of the known pharmaceutical solid is stored. The optical property can include, but is not limited to, a shape, a color, a geometric engraving, or a coplanar symbol. The prescription vial is illuminated with a first light source that is substantially transmitted by artifacts of the prescription vial and a first image is recorded. The prescription vial is then illuminated with a second light source that is substantially reflected by the artifacts and a second image is recorded. The second image is used to remove the effects of the artifacts in the first image and the first image is processed to find the optical property of the pharmaceutical solid. The optical property is compared to the stored optical properties that identify known pharmaceutical solids. The pharmaceutical solid is identified from this comparison.

In another embodiment, a pharmaceutical solid in a prescription vial is identified from an optical property using directional lighting to enhance or suppress two-dimensional or three-dimensional effects on the surface of the pharmaceutical solid. As above, for each known pharmaceutical solid, an optical property of the known pharmaceutical solid is stored. A first direction and a second direction are selected. The prescription vial is illuminated with a light from the first direction and a first image is recorded. The prescription vial is then illuminated with the light from the second direction and a second image is recorded. The first image and the second image are processed to find an optical property of the pharmaceutical solid. The optical property is compared to the stored optical properties that identify known pharmaceutical solids. The pharmaceutical solid is identified from this comparison.

In another embodiment, a pharmaceutical solid in a prescription vial is identified from an optical property of the pharmaceutical solid using one light source that includes a light frequency that effectively allows artifacts of the prescription vial to be removed. As above, for each known pharmaceutical solid, an optical property of the known pharmaceutical solid is stored. The prescription vial is illuminated with a light source that includes a light frequency that is substantially reflected by artifacts of the prescription vial. An image is recorded. Edges recorded in the image from the light frequency are used to remove the effects of the artifacts in the image and the image the image is processed to find an optical property of the pharmaceutical solid. A first comparison of the optical property to one or more of the plurality of stored known optical properties is performed. The identity of the pharmaceutical solid is determined from the first comparison.

Figure 1:
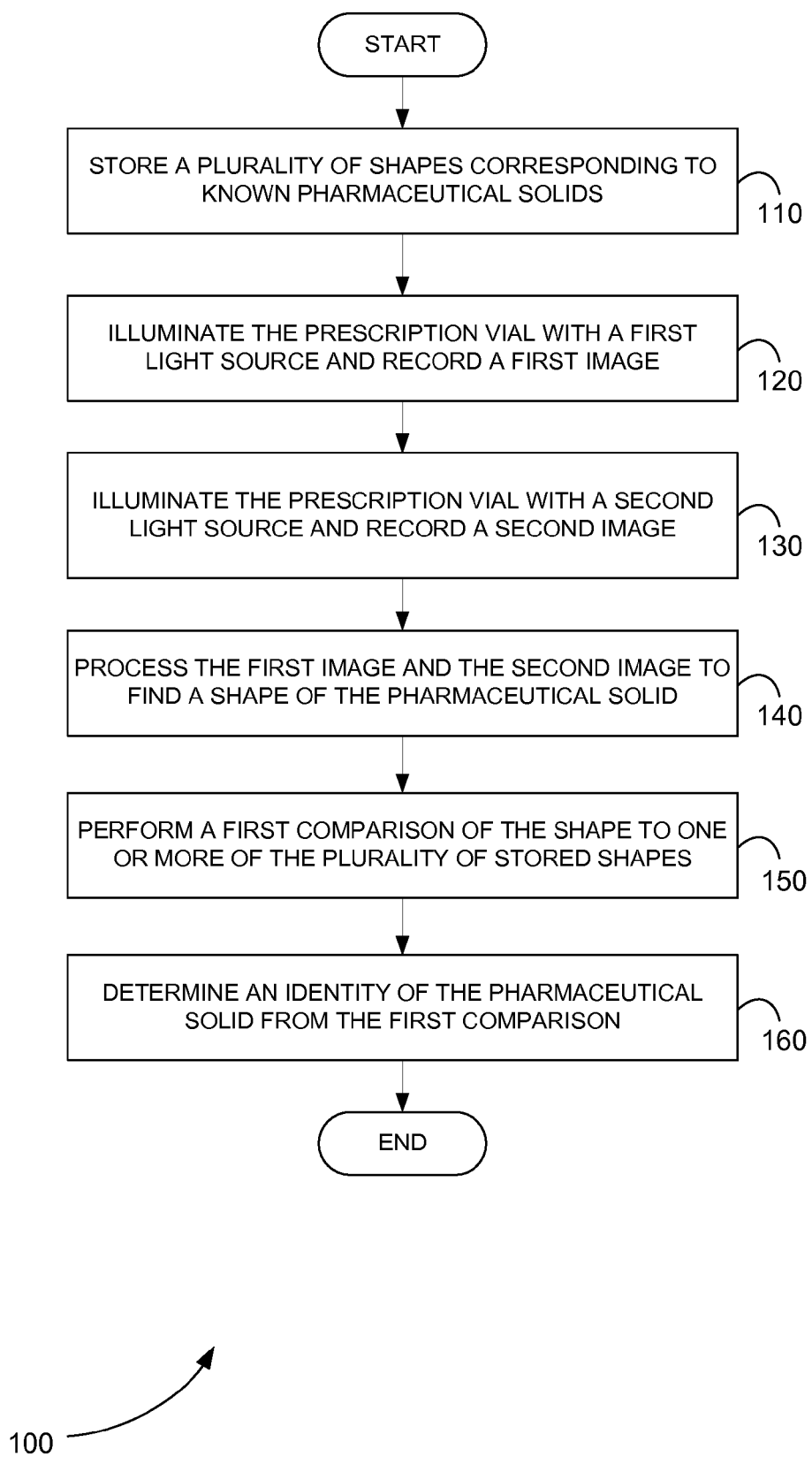
FIG. 1 is a flowchart showing a method for identifying a pharmaceutical solid in a prescription vial from the shape of the pharmaceutical solid using two different light sources, in accordance with an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

A system for communicating pharmaceutical verification information across a network is described in the '443 application. This pharmaceutical verification information includes at least one known spectral signature of a known pharmaceutical that is sent to an automatic prescription verification system across the network.

An automatic prescription verification system that uses spectroscopic analysis is described in the '395 patent. A system of the '395 patent uses a static multimode multiplex spectrometer (MMS). A static MMS is described in the '101 patent. A two-dimensional (2D) coded aperture static MMS is described in the '625 patent.

According to a system of the '395 patent, a standard prescription bottle or vial containing a pharmaceutical of a prescription is placed in the spectroscopic sensor system. The spectroscopic sensor system excites the Raman-active modes of the pharmaceutical and detects the resulting Raman emission. A spectral signature that is derived from the measurement is compared to one or more spectral signatures of known pharmaceuticals that are stored in a database. If the spectral signature of the pharmaceutical in the vial matches a spectral signature of a known pharmaceutical stored in the database, the pharmaceutical in the vial is identified. If the identity of the pharmaceutical in the vial matches the pharmaceutical of the prescription, the prescription is verified.

A system of the '395 patent may also include an imaging device to assist in uniquely identifying the pharmaceutical in the prescription vial. The spectral and imaging database may contain images of pharmaceuticals showing their size, shape, color and/or texture, or other data characterizing the size, shape, color and/or texture of known pharmaceuticals. For example, certain pharmaceutical tablets are provided in different sizes according to the dose of the pharmaceutical. In these cases, different doses of the same pharmaceutical may have the same spectral signature, such that the spectral signature cannot be used to identify the strength in addition to identifying the pharmaceutical itself. Once the pharmaceutical has been identified, the imaging device can then be used to identify the strength by comparing the size of the prescription tablet to the sizes for different strengths of that pharmaceutical in the spectral and image database. The imaging device can also be used to determine the shape and/or color of the tablets. This data can then be used as a double-check on the identity of the pharmaceutical, or to differentiate between different strengths or forms (tablets, caplets, liquids, pills, capsules, etc.) of the pharmaceuticals.

Embodiments of the present invention include methods for identifying a pharmaceutical solid in a prescription vial using machine vision. These methods can be used in conjunction with spectroscopic or other analysis techniques. These methods can also be used independently.

Using Two Different Light Sources

FIG. 1 is a flowchart showing a method 100 for identifying a pharmaceutical solid in a prescription vial from the shape of the pharmaceutical solid using two different light sources, in accordance with an embodiment of the present invention. A pharmaceutical solid is, for example, a pill. A pill can include, but is not limited to, a tablet, a caplet, a suppository, a gelcap, or a capsule.

In step 110 of method 100, a plurality of shapes corresponding to known pharmaceutical solids is stored.

In step 120, the prescription vial is illuminated with a first light source and a first image is recorded. The first light source can be, for example, an infrared light source.

In step 130, the prescription vial is illuminated with a second light source and a second image is recorded. The second light source can be, for example, a visible light source.

In step 140, the first image and the second image are processed to find a shape of the pharmaceutical solid.

In step 150, a first comparison of the shape to one or more of the plurality of stored shapes is performed.

In step 160, an identity of the pharmaceutical solid is determined from the first comparison.

In various embodiments, the first light can be a directional light source or a diffuse light source and the second light can be a directional light source or a diffuse light source. A directional light source can be used to determine three-dimensional characteristics of the pharmaceutical solid. A diffuse light source can be used to determine planar characteristics of the pharmaceutical solid.

In various embodiments, the first image and the second image can also be used to determine the amount of the pharmaceutical solid in the prescription vial.

In various embodiments, the first light source and the second light source illuminate the bottom of the prescription vial.

In various embodiments, edge detection is used to find shape information in the first image and the second image. Geometric patterns formed by edges in the first image and the second image that represent shapes of pharmaceutical solids are identified.

If the first image is obtained using an infrared light source, for example, grayscale statistics can be used to characterize a shape or geometric pattern in the first image. Grayscale statistics can include, but are not limited to, grayscale histogram statistics. After identifying a geometric pattern in a first location in the first image, grayscale statistics of the pixels in the geometric pattern can be used to create a score for the geometric pattern. Multi-pill information can be used to improve the reliability of the score. The same geometric pattern can be identified in a second location in the first image, and grayscale statistics of the pixels in the geometric pattern in the second location can be used to modify the original score.

Similarly, if the second image is obtained using a visible light source, color statistics can be used to characterize a shape or geometric pattern in the second image. Color statistics can include, but are not limited to, color histogram statistics. After identifying a geometric pattern in a first location in the second image, color statistics of the pixels in the geometric pattern can be used to create a score for the geometric pattern. Again, multi-pill information can be used to improve the reliability of the score. The same geometric pattern can be identified in a second location in the second image, and color statistics of the pixels in the geometric pattern in the second location can be used to modify the original score.

Because visible light has multiple frequencies or channels, edge detection can include accumulating the edges of multiple channels. For example, the second image can be analyzed using a color space, and, for each channel of the color space edges can be identified, the identified edges from the each channel can be accumulated, and the accumulated edges can be combined into geometric patterns of the second image. Color spaces that can be used include, but are not limited to, red, green, blue (RGB), lightness and a and b for color-opponent dimensions (Lab), or hue/saturation/intensity (HSI).

Accumulating the edges for separate channels of a color space can be useful in removing artifacts of the prescription vial. These artifacts can include, but are not limited to, lettering on the prescription vial, indentations in the prescription vial, or debris on the prescription vial. For example, accumulated edges from color channels that are substantially transmitted by artifacts of the prescription vial can be added to geometric patterns processed from the second image, while edges from color channels that are substantially reflected by the artifacts can be subtracted from the geometric patterns processed from the second image. Removing artifacts of the prescription vial are discussed in more detail in the next section.

In various embodiments, method 100 can be used in conjunction with spectroscopic analysis of the pharmaceutical solid. For example, a plurality of spectral signatures corresponding to the known pharmaceutical solids can be stored. A spectral signature of the pharmaceutical solid can be measured using a multimode multiplex spectrometer (MMS). A second comparison of the measured spectral signature to one or more of the plurality of stored spectral signatures can be performed. Finally, the identity of the pharmaceutical solid can be determined from the second comparison in addition to the first comparison. The identity of the pharmaceutical solid can be determined by selecting a known pharmaceutical solid that most closely matches the shape found from processing the first image and the second image in method 100 and the measured spectral signature that was found using the MMS, for example.

In various embodiments, spectroscopic analysis can be used to prescreen known pharmaceutical solids for the first comparison in method 100. For example, the second comparison of the measured spectral signature to one or more of the plurality of stored spectral signatures in spectroscopic analysis can be used to produce one or more known pharmaceutical solids that match the measured spectral signature. The one or more known pharmaceutical solids that are produced can be used to select the one or more of the plurality of stored shapes used in the first comparison of method 100.

Alternatively, method 100 can be used to prescreen known pharmaceutical solids for the second comparison that is based on spectroscopic analysis. For example, the first comparison of the shape to one or more of the plurality of stored shapes in method 100 can be used to produce one or more known pharmaceutical solids that match the shape. The one or more known pharmaceutical solids produced can then be used to select the one or more of the plurality of stored spectral signatures used in the second comparison.

Method 100 can also be used to aid spectroscopic analysis in other ways. For example, the first image and the second image found in method 100 can be used to determine a location to direct a laser of the MMS. Directing the laser of the spectrometer to a specific pharmaceutical solid can improve the efficiency and reliability of the spectroscopic analysis.

In various embodiments, method 100, which involves identifying a shape of the pharmaceutical solid, can be used in conjunction with a machine vision technique that identifies a color of the pharmaceutical solid. For example, a plurality of colors corresponding to the known pharmaceutical solids can be stored. The second image of method 100 can be used to find a color of the pharmaceutical solid. The second image can be obtained from a visible light source, for example. A second comparison of the color to one or more of the plurality of stored colors can be performed. Finally, the identity of the pharmaceutical solid can be determined from the second comparison in addition to the first comparison of method 100.

In various embodiments, the color of a pharmaceutical solid can be found from the light reflected from an area in the prescription vial rather than from specifically identified pills or capsules. Since artifacts of the prescription vial can affect the light reflected from such an area, it is important that this area be selected carefully. For example, processing the second image of method 100 to find color can include selecting pixels from a portion of the second image that correspond to a portion of the prescription vial substantially free of artifacts of the prescription vial and statistically correlating color information in each of the selected pixels to determine the color.

In various embodiments, method 100, which involves identifying a shape of the pharmaceutical solid, can be used in conjunction with a machine vision technique that identifies a geometric engraving on the pharmaceutical solid. For example, a plurality of geometric engravings corresponding to the known pharmaceutical solids can be stored. The first image found in method 100 can be used to find a geometric engraving on the pharmaceutical solid. The first image can be obtained from an infrared light source, for example. A second comparison of the geometric engraving to one or more of the plurality of stored geometric engravings can be performed. Finally, the identity of the pharmaceutical solid can be determined from the second comparison in addition to the first comparison of method 100.

A geometric engraving on a pharmaceutical solid can include an indentation for identification. Such an indentation can identify the pharmaceutical, the strength, or the manufacturer, for example. A geometric engraving on a pharmaceutical solid can also include an indentation for a function other than identification. For example, a pill can be indented in order to allow the pill to be easily broken into two or more pieces. The edge in the center of a capsule can also be considered as an indentation for a function other than identification.

In various embodiments, method 100, which involves identifying a shape of the pharmaceutical solid, can be used in conjunction with a machine vision technique that identifies a coplanar symbol on the pharmaceutical solid. For example, a plurality of coplanar symbols corresponding to the known pharmaceutical solids can be stored. The second image found in method 100 can be used to find a coplanar symbol on the pharmaceutical solid. The second image can be obtained from a visible light source, for example. A second comparison of the coplanar symbol to one or more of the plurality of stored coplanar symbols can be performed. Finally, the identity of the pharmaceutical solid can be determined from the second comparison in addition to the first comparison of method 100.

A coplanar symbol can be an identifier on the pharmaceutical solid that adds no substantial height to the surface of the pharmaceutical solid. The identifier can identify the pharmaceutical, the strength, or the manufacturer, for example. The identifier can be a printed symbol on the pharmaceutical solid, for example.

Removing Artifacts of the Prescription Vial

The use of a multimode multiplex spectrometer (MMS) allows pharmaceutical solids to be analyzed through a prescription vial. In other words, the light analyzed by the MMS passes back and forth through the prescription vial and there is no need to remove the cap of the prescription vial. Similarly, in various embodiments, machine vision is used to analyze the shape, color, geometric engravings, and coplanar symbols of pharmaceutical solids through the prescription vial. As mentioned above, in various embodiments, machine vision can remove artifacts of the prescription vial using two different light sources.

Figure 2:
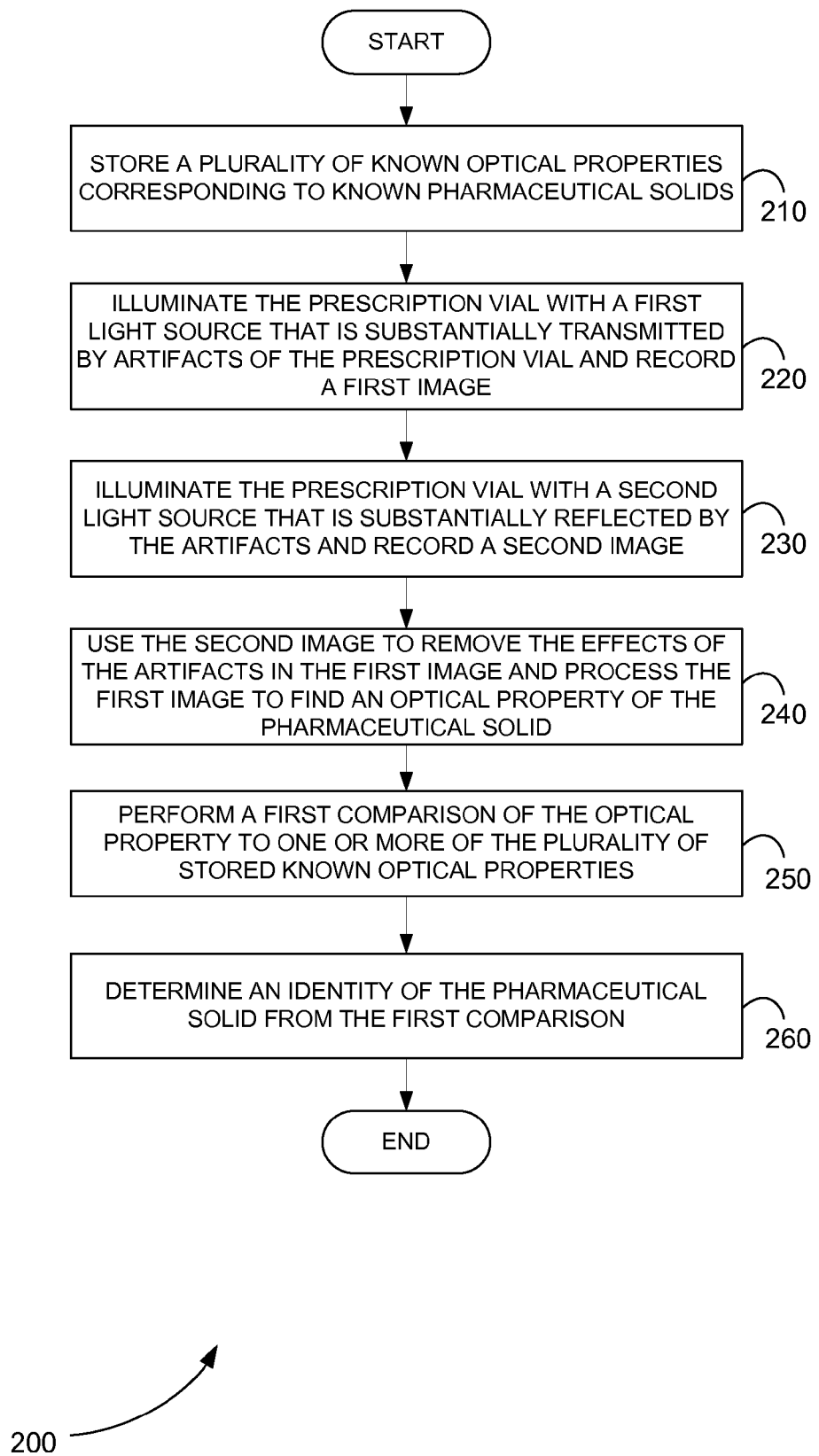
FIG. 2 is a flowchart showing a method for identifying a pharmaceutical solid in a prescription vial by removing artifacts of the prescription vial using two different light sources, in accordance with an embodiment of the present invention.

FIG. 2 is a flowchart showing a method 200 for identifying a pharmaceutical solid in a prescription vial by removing artifacts of the prescription vial using two different light sources, in accordance with an embodiment of the present invention.

In step 210 of method 200, a plurality of known optical properties corresponding to known pharmaceutical solids is stored.

In step 220, the prescription vial is illuminated with a first light source that is substantially transmitted by artifacts of the prescription vial and a first image is recorded.

In step 230, the prescription vial is illuminated with a second light source that is substantially reflected by the artifacts and a second image is recorded.

In step 240, the second image is used to remove the effects of the artifacts in the first image and the first image is processed to find an optical property of the pharmaceutical solid.

In step 250, a first comparison of the optical property to one or more of the plurality of stored known optical properties is performed.

In step 260, the identity of the pharmaceutical solid is determined from the first comparison.

In various embodiments, the prescription vial can include an amber vial, the second light source can include an ultraviolet source, and the first light source can include at least one light source other than an ultraviolet light source.

In various embodiments the plurality of known optical properties corresponding to known pharmaceutical solids can include, but is not limited to, a plurality of known shapes, a plurality of known colors, a plurality of known geometric engravings, and a plurality of known coplanar symbols and the optical property found can be, but is not limited to, a shape, a color, a geometric engraving, or a coplanar symbol, respectively.

In various embodiments, method 200 can also be used in conjunction with spectroscopic analysis of the pharmaceutical solid. For example, a plurality of spectral signatures corresponding to the known pharmaceutical solids can be stored. A spectral signature of the pharmaceutical solid can be measured using an MMS. A second comparison of the measured spectral signature to one or more of the plurality of stored spectral signatures can be performed. Finally, the identity of the pharmaceutical solid can be determined from the second comparison in addition to the first comparison. The identity of the pharmaceutical solid can be determined by selecting a known pharmaceutical solid that most closely matches the shape found from processing the first image and the second image in method 200 and the measured spectral signature that was found using the MMS, for example.

Using Light from Two Different Directions

Both two-dimensional and three-dimensional optical properties can be used to identify pharmaceutical solids. In various embodiments, directional lighting can be used to enhance or suppress two-dimensional or three-dimensional effects depending on the optical property of interest.

Figure 3:
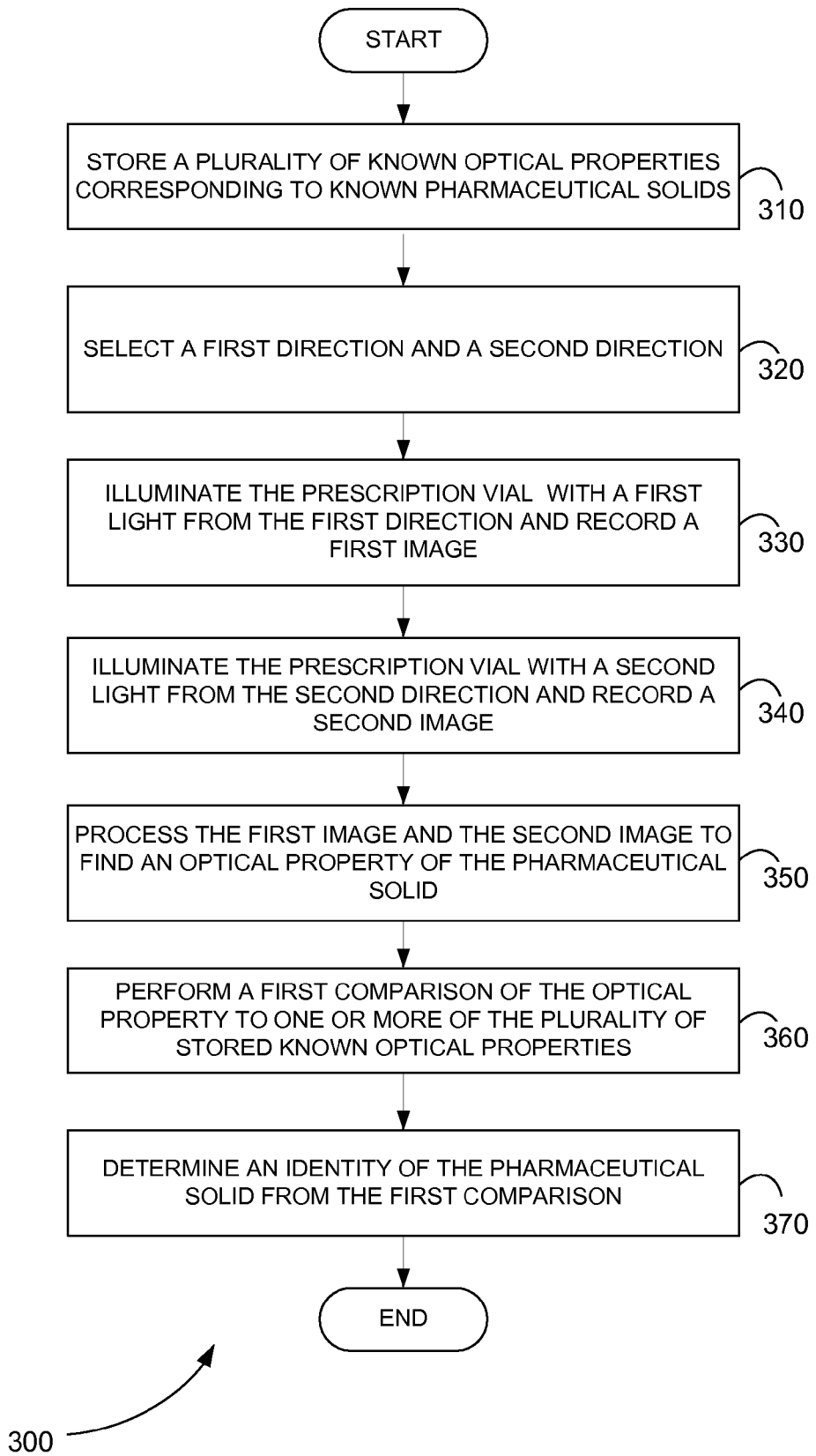
FIG. 3 is a flowchart showing a method for identifying a pharmaceutical solid in a prescription vial using light from two different directions, in accordance with an embodiment of the present invention.

FIG. 3 is a flowchart showing a method 300 for identifying a pharmaceutical solid in a prescription vial using light from two different directions, in accordance with an embodiment of the present invention.

In step 310 of method 300, a plurality of known optical properties corresponding to known pharmaceutical solids is stored.

In step 320, a first direction and a second direction are selected.

In step 330, the prescription vial is illuminated with a first light from the first direction and a first image is recorded.

In step 340, the prescription vial is illuminated with a second light from the second direction and a second image is recorded. The first light and the second light can be the same light, for example. In various embodiments, the first light and the second light are different frequencies of light.

In step 350, the first image and the second image are processed to find an optical property of the pharmaceutical solid.

In step 360, a first comparison of the optical property to one or more of the plurality of known optical properties is performed.

In step 370, the identity of the pharmaceutical solid is determined from the first comparison.

In various embodiments, the two-dimensional or three-dimensional effects are enhanced or suppressed by the selection of the first direction and the second direction in method 300. For example, three-dimensional effects can be enhanced and two-dimensional effects can be suppressed by selecting the first direction and the second direction to maximize areas of maximum reflectivity and maximize areas of minimum reflectivity in the first image and the second image. Alternatively, three-dimensional effects can be suppressed and two-dimensional effects can be enhanced by selecting the first direction and the second direction to minimize areas of maximum reflectivity and minimize areas of minimum reflectivity in the first image and the second image. An area of maximum reflectivity can be a glint, for example. An area of minimum reflectively can be a shadow, for example.

As above, in various embodiments the plurality of known optical properties corresponding to known pharmaceutical solids can include, but is not limited to, a plurality of known shapes, a plurality of known colors, a plurality of known geometric engravings, and a plurality of known coplanar symbols and the optical property found can be, but is not limited to, a shape, a color, a geometric engraving, or a coplanar symbol, respectively. Shape and geometric engraving are three-dimensional effects and color and coplanar symbols are two-dimensional effects, for example.

Also as above, in various embodiments, method 300 can be used in conjunction with spectroscopic analysis of the pharmaceutical solid. For example, a plurality of spectral signatures corresponding to the known pharmaceutical solids can be stored. A spectral signature of the pharmaceutical solid can be measured using an MMS. A second comparison of the measured spectral signature to one or more of the plurality of stored spectral signatures can be performed. Finally, the identity of the pharmaceutical solid can be determined from the second comparison in addition to the first comparison. The identity of the pharmaceutical solid can be determined by selecting a known pharmaceutical solid that most closely matches the shape found from processing the first image and the second image in method 300 and the measured spectral signature that was found using the MMS, for example.

Using One Light Source

In various embodiments, machine vision using a single light source can be used to remove artifacts of the prescription vial and analyze the shape, color, geometric engravings, and coplanar symbols of pharmaceutical solids through the prescription vial. The single light source incident on the prescription vial includes a light frequency that is substantially reflected by artifacts of the prescription vial. An image is recorded from the light reflected from the prescription vial and its contents. The image is divided into images from different frequency channels. An image from the channel recording light from the light frequency that is substantially reflected by artifacts of the prescription vial is combined with one or more images from one or more different channels to remove the artifacts of the prescription vial and determine a shape, color, geometric engraving, or coplanar symbol of a pharmaceutical solid in the prescription vial.

Figure 4:
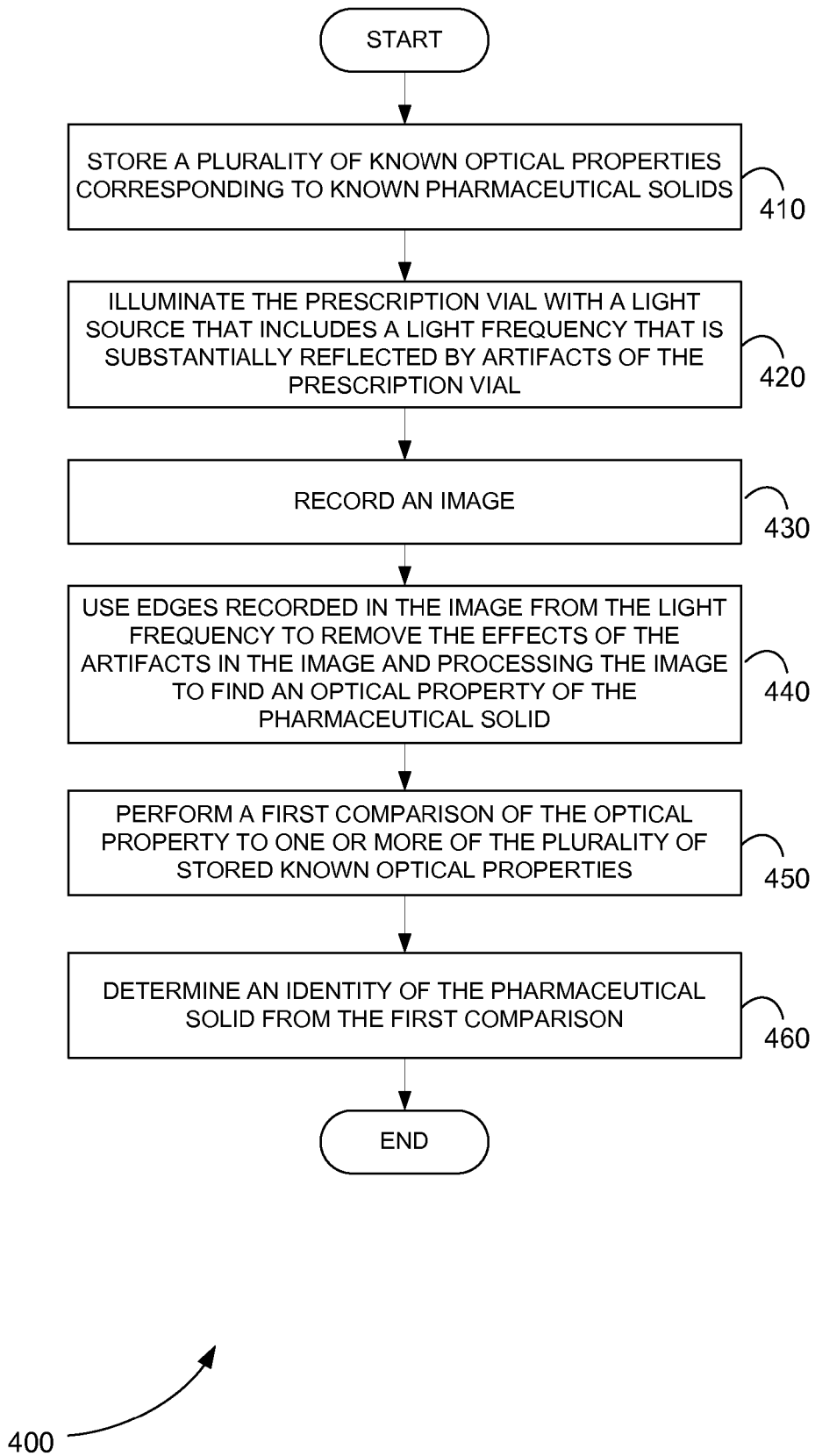
FIG. 4 is a flowchart showing a method for identifying a pharmaceutical solid in a prescription vial by removing artifacts of the prescription vial using one light source, in accordance with an embodiment of the present invention.

FIG. 4 is a flowchart showing a method 400 for identifying a pharmaceutical solid in a prescription vial by removing artifacts of the prescription vial using one light source, in accordance with an embodiment of the present invention.

In step 410 of method 400, a plurality of known optical properties corresponding to known pharmaceutical solids is stored.

In step 420, the prescription vial is illuminated with a light source that includes a light frequency that is substantially reflected by artifacts of the prescription vial.

In step 430, an image is recorded.

In step 440, edges recorded in the image from the light frequency are used to remove the effects of the artifacts in the image and the image is processed to find an optical property of the pharmaceutical solid.

In step 450, a first comparison of the optical property to one or more of the plurality of stored known optical properties is performed.

In step 460, an identity of the pharmaceutical solid is determined from the first comparison.

As above, in various embodiments the plurality of known optical properties corresponding to known pharmaceutical solids can include, but is not limited to, a plurality of known shapes, a plurality of known colors, a plurality of known geometric engravings, and a plurality of known coplanar symbols and the optical property found can be, but is not limited to, a shape, a color, a geometric engraving, or a coplanar symbol, respectively.

In accordance with an embodiment of the present invention, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed. The terms "instructions configured to be executed" and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for identifying a pharmaceutical solid in a closed prescription vial, comprising:
   storing a plurality of known optical properties corresponding to known pharmaceutical solids;
   illuminating the closed prescription vial with a first light source that is substantially transmitted by artifacts of the closed prescription vial and recording a first image through the closed prescription vial using an imaging device, wherein artifacts of the closed prescription vial include lettering on the prescription vial or indentations in the closed prescription vial;
   illuminating the closed prescription vial with a second light source that is substantially reflected by the artifacts and recording a second image through the closed prescription vial using the imaging device;
   illuminating the closed prescription vial with a third light source and recording a third image through the closed prescription vial using an imaging device;
   illuminating the closed prescription vial with a fourth light source and recording a fourth image through the closed prescription vial using the imaging device;
   using the second image to remove the effects of the artifacts in the first image and processing the first image, the third image, and the fourth image to find an optical property of the pharmaceutical solid;
   performing a first comparison of the optical property to one or more of the plurality of stored optical properties; and
   determining, using a processor, an identity of the pharmaceutical solid from the first comparison.

2. The method of claim 1, wherein the third light source comprises a directional light source and the fourth light source comprises a diffuse light source.

3. The method of claim 1, wherein the third light source comprises infrared light source.

4. The method of claim 1, wherein the fourth light source comprises visible light source.

5. The method of claim 4, further comprising
   storing a plurality of colors corresponding to the known pharmaceutical solids,
   processing the fourth image to find a color of the pharmaceutical solid,
   performing a second comparison of the color to one or more of the plurality of stored colors, and
   determining the identity of the pharmaceutical solid from the second comparison in addition to the first comparison.

6. The method of claim 5, wherein processing the fourth image to find the color comprises
   selecting pixels from a portion of the fourth image that correspond to a portion of the prescription vial substantially free of artifacts of the prescription vial and
   statistically correlating color information in each of the selected pixels to determine the color.

7. The method of claim 1, wherein the pharmaceutical solid comprises a pill.

8. The method of claim 1, wherein the pharmaceutical solid comprises a capsule.

9. The method of claim 1, further comprising using the third image and the fourth image to determine an amount of the pharmaceutical solid in the prescription vial.

10. The method of claim 1, wherein illuminating the prescription vial with a third light source comprises illuminating a bottom of the prescription vial with the third light source and wherein illuminating the prescription vial with a fourth light source comprises illuminating the bottom of the prescription vial with the fourth light source.

11. The method of claim 1, wherein processing the third image and the fourth image to find the optical property comprises identifying geometric patterns formed by edges in the third image and the fourth image that represent shapes of pharmaceutical solids.

12. The method of claim 11, further comprising identifying a geometric pattern in a first location in the third image and using grayscale statistics of pixels in the geometric pattern to create a score for the geometric pattern.

13. The method of claim 12, further comprising identifying the geometric pattern in a second location in the third image and using grayscale statistics of pixels in the geometric pattern in the second location to modify the score.

14. The method of claim 11, further comprising selecting a geometric pattern from the identified geometric patterns in a first location in the fourth image and using color statistics of pixels in the geometric pattern to create a score for the geometric pattern.

15. The method of claim 14, further comprising selecting the geometric pattern in a second location in the fourth image and using color statistics of pixels in the geometric pattern to modify the score.

16. The method of claim 11, further comprising analyzing the fourth image using a color space and for each channel of the color space identifying edges, accumulating the identified edges from the each channel, and combining the accumulated edges into the identified geometric patterns.

17. The method of claim 16, wherein combining the accumulated edges into the identified geometric patterns comprises adding edges from color channels that are substantially transmitted by artifacts of the prescription vial and subtracting edges from color channels that are substantially reflected by the artifacts.

18. The method of claim 17, wherein the artifacts comprise one or more of lettering on the prescription via, indentations in the prescription vial, and debris on the prescription vial.

19. The method of claim 1, further comprising
   storing a plurality of spectral signatures corresponding to the known pharmaceutical solids,
   measuring a spectral signature of the pharmaceutical solid using a multimode multiplex spectrometer,
   performing a second comparison of the measured spectral signature to one or more of the plurality of stored spectral signatures, and
   determining the identity of the pharmaceutical solid from the second comparison in addition to the first comparison.

20. The method of claim 19, wherein determining the identity of the pharmaceutical solid from the first comparison in addition to the second comparison comprises selecting a known pharmaceutical solid that most closely matches the optical property and the measured spectral signature.

21. The method of claim 19, further comprising using the second comparison to produce one or more known pharmaceutical solids that match the measured spectral signature and using the one or more known pharmaceutical solids to select the one or more of the plurality of stored optical properties used in the first comparison.

22. The method of claim 19, further comprising using the first comparison to produce one or more known pharmaceutical solids that match the optical property and using the one or more known pharmaceutical solids to select the one or more of the plurality of stored spectral signatures used in the second comparison.

23. The method of claim 19, further comprising using the third image and the fourth image to determine a location to direct a laser of the multimode multiplex spectrometer.

24. The method of claim 1, further comprising
storing a plurality of geometric engravings corresponding to the known pharmaceutical solids,
processing the third image to find a geometric engraving on the pharmaceutical solid,
performing a second comparison of the geometric engraving to one or more of the plurality of stored geometric engravings, and
determining the identity of the pharmaceutical solid from the second comparison in addition to the first comparison.

25. The method of claim 24, wherein the geometric engraving comprises an indentation for identification.

26. The method of claim 24, wherein the geometric engraving comprises an indentation for a function other than identification.

27. The method of claim 1, further comprising
storing a plurality of coplanar symbols corresponding to the known pharmaceutical solids,
processing the fourth image to find a coplanar symbol on the pharmaceutical solid,
performing a second comparison of the geometric engraving to one or more of the plurality of stored coplanar symbols, and
determining the identity of the pharmaceutical solid from the second comparison in addition to the first comparison.

28. The method of claim 27, wherein the coplanar symbol comprises a printed symbol on the pharmaceutical solid.

29. The method of claim 1, wherein the first light source is the third light source and the second light source is the fourth light source.

30. A method for identifying a pharmaceutical solid in a closed prescription vial, comprising:
storing a plurality of known optical properties corresponding to known pharmaceutical solids;
illuminating the closed prescription vial with a first light source that is substantially transmitted by artifacts of the closed prescription vial and recording a first image through the closed prescription vial using an imaging device, wherein artifacts of the closed prescription vial include lettering on the prescription vial or indentations in the closed prescription vial;
illuminating the closed prescription vial with a second light source that is substantially reflected by the artifacts and recording a second image through the closed prescription vial using the imaging device;
using the second image to remove the effects of the artifacts in the first image and processing the first image to find an optical property of the pharmaceutical solid;
performing a first comparison of the optical property to one or more of the plurality of stored known optical properties; and
determining, using a processor, an identity of the pharmaceutical solid from the first comparison.

31. The method of claim 30, wherein the prescription vial comprises an amber vial.

32. The method of claim 30, wherein the plurality of known optical properties corresponding to known pharmaceutical solids comprises a plurality of known shapes corresponding to known pharmaceutical solids and the optical property comprises a shape.

33. The method of claim 30, wherein the plurality of known optical properties corresponding to known pharmaceutical solids comprises a plurality of known colors corresponding to known pharmaceutical solids and the optical property comprises a color.

34. The method of claim 30, wherein the plurality of known optical properties corresponding to known pharmaceutical solids comprises a plurality of known geometric engravings corresponding to known pharmaceutical solids and the optical property comprises a geometric engraving.

35. The method of claim 30, wherein the plurality of known optical properties corresponding to known pharmaceutical solids comprises a plurality of known coplanar symbols corresponding to known pharmaceutical solids and the optical property comprises a coplanar symbol.

36. The method of claim 30, further comprising
storing a plurality of spectral signatures corresponding to the known pharmaceutical solids,
measuring a spectral signature of the pharmaceutical solid using a multimode multiplex spectrometer,
performing a second comparison of the measured spectral signature to one or more of the plurality of stored spectral signatures, and
determining an identity of the pharmaceutical solid from the second comparison in addition to the first comparison.

37. A method for identifying a pharmaceutical solid in a closed prescription vial, comprising:
storing a plurality of known shapes corresponding to known pharmaceutical solids;
selecting a first direction and a second direction;
illuminating the closed prescription vial with a first light source that is substantially transmitted by artifacts of the closed prescription vial and recording a first image through the closed prescription vial using an imaging device, wherein artifacts of the closed prescription vial include lettering on the prescription vial or indentations in the closed prescription vial;
illuminating the closed prescription vial with a second light source that is substantially reflected by the artifacts and recording a second image through the closed prescription vial using the imaging device;
illuminating the closed prescription vial with a third light from the first direction and recording a third image through the closed prescription vial using an imaging device;
illuminating the closed prescription vial with a fourth light from the second direction and recording a fourth image through the closed prescription vial using the imaging device;
using the second image to remove the effects of the artifacts in the first image and processing the first image, the third image, and the fourth image to find a shape of the pharmaceutical solid;
performing a first comparison of the shape to one or more of the plurality of known shapes; and
determining, using a processor, an identity of the pharmaceutical solid from the first comparison.

38. The method of claim 37, further comprising selecting the first direction and the second direction to maximize areas of maximum reflectivity and maximize areas of minimum reflectivity in the third image and the fourth image.

39. The method of claim 37, further comprising selecting the first direction and the second direction to minimize areas of maximum reflectivity and minimize areas of minimum reflectivity in the third image and the fourth image.

40. The method of claim 37, further comprising storing a plurality of known optical properties corresponding to known pharmaceutical solids and processing the third image and the fourth image to find an optical property of the pharmaceutical solid in addition to shape.

41. The method of claim 40, wherein the plurality of known optical properties corresponding to known pharmaceutical solids comprises a plurality of known colors corresponding to known pharmaceutical solids and the optical property comprises a color.

42. The method of claim 40, wherein the plurality of known optical properties corresponding to known pharmaceutical solids comprises a plurality of known geometric engravings corresponding to known pharmaceutical solids and the optical property comprises a geometric engraving.

43. The method of claim 40, wherein the plurality of known optical properties corresponding to known pharmaceutical solids comprises a plurality of known coplanar symbols corresponding to known pharmaceutical solids and the optical property comprises a coplanar symbol.

44. The method of claim 37, further comprising
   storing a plurality of spectral signatures corresponding to the known pharmaceutical solids,
   measuring a spectral signature of the pharmaceutical solid using a multimode multiplex spectrometer,
   performing a second comparison of the measured spectral signature to one or more of the plurality of stored spectral signatures, and
   determining an identity of the pharmaceutical solid from the second comparison in addition to the first comparison.

45. The method of claim 37, wherein the first light source is the third light source and the second light source is the fourth light source.

46. A method for identifying a pharmaceutical solid in a closed prescription vial, comprising:
   storing a plurality of known optical properties corresponding to known pharmaceutical solids;
   illuminating the closed prescription vial with a light source that includes a light frequency that is substantially reflected by artifacts of the closed prescription vial, wherein artifacts of the closed prescription vial include lettering on the prescription vial or indentations in the closed prescription vial;
   recording an image through the closed prescription vial using an imaging device;
   using edges recorded in the image from the light frequency to remove the effects of the artifacts in the image and processing the image to find an optical property of the pharmaceutical solid;
   performing a first comparison of the optical property to one or more of the plurality of stored known optical properties; and
   determining, using a processor, an identity of the pharmaceutical solid from the first comparison.

47. The method of claim 46, further comprising
   storing a plurality of spectral signatures corresponding to the known pharmaceutical solids,
   measuring a spectral signature of the pharmaceutical solid using a multimode multiplex spectrometer,
   performing a second comparison of the measured spectral signature to one or more of the plurality of stored spectral signatures, and
   determining an identity of the pharmaceutical solid from the second comparison in addition to the first comparison.

* * * * *